| United States Patent [19] | [11] Patent Number: 4,725,355 |
| Yamamoto et al. | [45] Date of Patent: Feb. 16, 1988 |

[54] BODY FLUID PURIFICATION MEDIUM AND APPARATUS

[75] Inventors: Yuichi Yamamoto; Tadashi Sameshima, both of Fujinomiya, Japan

[73] Assignee: Terumo Kabushiki Kaisha, Tokyo, Japan

[21] Appl. No.: 762,293

[22] Filed: Aug. 5, 1985

[30] Foreign Application Priority Data

Aug. 7, 1984 [JP] Japan .................................. 59-165454

[51] Int. Cl.$^4$ ............................................. B01D 27/02
[52] U.S. Cl. ..................................... 210/266; 210/287; 210/502.1; 210/506; 502/401
[58] Field of Search ............... 210/263, 264, 927, 266, 210/291, 195.2, 287, 502.1, 506; 502/401

[56] References Cited

U.S. PATENT DOCUMENTS 4,331,728  5/1982  Theeuwes ..................... 210/500.42
4,432,871  2/1984  Yamawaki et al. ............. 210/927 X

FOREIGN PATENT DOCUMENTS

57-122875  7/1982  Japan .
59-17355   1/1984  Japan .
59-17356   1/1984  Japan .

Primary Examiner—Richard V. Fisher
Assistant Examiner—W. Gary Jones
Attorney, Agent, or Firm—Burns, Doane, Swecker & Mathis

[57] ABSTRACT

A body fluid purification medium comprises a support, and an adsorbent including at least one sulfa drug and fixed on a surface of said insoluble support for adsorbing and removing a pathogenic substance in a body fluid. The medium can be provided in a body fluid flow path provided in a container between body fluid inlet and outlet ports.

33 Claims, 2 Drawing Figures

BODY FLUID PURIFICATION MEDIUM AND APPARATUS

BACKGROUND OF THE INVENTION

1. Field of the Invention

The present invention relates to a body fluid purification medium and a body fluid purification apparatus using the medium for therapeutic purposes of hepatic insufficiency, autoimmune diseases, renal diseases, myoneural diseases, blood dyscrasia, endocrinopathy, cacochymia, allergies, and rejections upon organ transplantation. Body fluids herein include blood, lymphocytes, ascites and the like, but the following description will be made mainly with reference to the case of blood.

II. Description of the Prior Art

When a humoral or cellular immune response against an antigen of cells or tissues of a patient occurs to produce an autoantibody, a disease is caused or a disease accompanying such an immune reaction is caused. Such a disease is called an autoimmune disease. Since a method for preventing such a diseases has not been established, efforts are being made to reduce production of an autoantibody and inflammation of tissues to a minimum. For this purpose, aspirin, drugs called indomethacin for suppressing inflammation, adrenocortical hormones, or drugs for suppressing an immune reaction, i.e., immunosuppressive agents (e.g., imuran, endoxan, or methotrexate) are used. In general, administration of adrenocortical hormones frequently provides good effects. However, when adrenocortical hormones are administered in large amounts over an extended period of time, resistance against infection is lowered and occurrence of stomach or duodenal ulcers, bone weakening (osteoporosis), atrophy of the adrenal cortex, myonosus, diabetes, or psychoneurosis is cortex, myonosus, diabetes, or psychoneurosis is common. Thereafter, administered amounts and time period must be reduced to a minimum. On the other hand, immunosuppressive agents contain carcinogens and damage the hematopoietic function, causing hepatopathy or digestive organ disease.

Plasma exchange therapy for eliminating certain types of immunoglobulin and immune complex has recently been adopted. Such immunoglobulin and immune complexes are considered to be closely associated with causes and the course of diseases associated with immunological functions, including monoclonal proteinemia, allergies, autoimmune diseases, immunodeficiency, or cancers.

However, in plasma exchange therapy, since all the plasma components are equally eliminated, not only loss of necessary plasma components occurs, but also supply shortage of plasma or plasma preparations and the accompanying problems of serum hepatitis or allergies occur. In view of these problems, it is recommended the plasma of a patient be restored after purification.

The methods of eliminating a pathogenic substance include the cascade method using a membrane filter (Sieberth, H.G., Plasma Exchange, p. 29, F. K. Schattauer, Verlag, Stuttgart-New York, 1980), the double filtration method (Tetsuzo Agishi et al, "Jin to Toseki", 10(3), 475, 1981), the freezing filtration method (L'Abbate, A., et al., Proc. Eur. Dial. Transplant. Assoc., 14, 486, 1977), and the salting-out method (Hiroaki Ooe, "Jinkou Zoki", 14, 472, 1985). Clinical tests of these methods are being performed. However, an ideal plasma fractionator (plasma protein fractionator) has not been obtained. When a plasma replenishing liquid is not used in clinical application, hypoproteinemia develops. Therefore, development of an ideal plasma filter and an adsorption medium capable of selectively adsorbing a specific pathogenic substance in plasma and of purifying the plasma has been strongly desired.

As a blood purification adsorbent, activated carbon, a styrene-divinylbenzene copolymer (AR-I) and a negative ion exchange resin has been proposed as an artificial liver support or an adsorption type artificial kidney.

However, such a substance does not have a capacity for adsorbing proteins of relatively large molecular weights in plasma, and development of an adsorbent of better quality is desired.

Conventional adsorbents intended for this purpose include:

(1) Affinity adsorbents (2) Organic porous resins such as an acrylic ester porous resin (e.g., "XAD-7" available from Rohm & Haas Co.) or a methacrylic ester porous resin (3) Ion exchange materials such as carboxymethyl cellulose (4) Inorganic porous materials such as porous silica or porous alumina However, an acrylic ester porous resin and carboxymethyl cellulose have poor absorption performance and specificity. They also adsorb albumins in a body fluid. Therefore, these adsorbents cause an abnormal osmotic pressure and cannot be used safely in therapeutic equipment.

Affinity adsorbents are roughly classified into biological and physicochemical affinity adsorbents. Biological affinity adsorbents have excellent adsorption specificity, however, they are expensive due to the use of physiologically active high-molecular weight substances such as ligands (i.e., substances having affinity with target substances). In addition, these biological affinity adsorbents have problems of sourcing, or the manufacture, sterilization, storage, transportation and stability of active life during storage and the like of adsorbents or columns. Furthermore, adverse side effects of other physiological functions other than affinity which appear upon contact with blood must also be considered. When a ligand is released and elutes, since it mostly consists of different types of proteins, the problem of side effects by antigens arises. Prevention of the introduction of endotoxins is also an important problem.

On the other hand, physicochemical affinity adsorbents can be mass-produced and have stable activity. These adsorbents also normally have excellent stability upon contact with blood.

Japanese Patent Disclosure (Kokoku) No. 57-122875 discloses an adsorbent for an immunoglobulin and/or immunoglobulin complex. The adsorbent includes a hydrophobic compound which is bonded with an insoluble support. Japanese Patent Disclosure No. 59-17355 discloses an adsorbent for an autoantibody and/or immune complex. The adsorbent includes an organic low-molecular weight compound containing a hydrophobic compound. The low-molecular weight compound is bonded with a porous substance having silanol groups on its surface. Examples of hydrophobic compounds include those having aromatic rings, nitrogen-containing 6-membered rings, nitrogen-containing 5-membered rings, polyvalent nitrogen-containing 6-membered rings, polyvalent nitrogen-containing 5-membered rings, oxygen-containing aromatic rings, sulfur-containing aromatic rings, oxygen-containing heterocylic aromatic rings, and sulfur-containing heterocylic aromatic rings.

However, conventional adsorbents have poor adsorption specificity and performance. In order to perform extracorporeal blood purification therapy when treating a patient, it is preferably that a pathogenic substance be eliminated at a still higher efficiency and adverse influences on the blood be extremely small.

SUMMRY OF THE INVENTION

It is an object of the present invention to provide a body fluid purification medium and a body fluid purification apparatus, wherein a pathogenic substance such as plasma proteins (e.g., immunoglobulins and immune complexes) can be selectively adsorbed with a high efficiency, non-specific adsorption is minimum, safety is guaranteed, sterilization is simple, and body fluid purification and regeneration can be optimally performed.

According to a first aspect of the present invention, there is provided a body fluid purification medium comprising:

a support; and
an adsorbent of a pathogenic substance fixed on a surface of the support and including at least one sulfa drug.

According to a second aspect of the present invention, there is provided a body fluid purification apparatus comprising:

a container having inlet and outlet ports for a body fluid and a body flow path provided between said ports; and
a body fluid purification medium provided in the flow path of the container, the medium comprising a support and an adsorbent of a pathogenic substance fixed on a surface of the support and including at least one sulfa drug.

According to a preferred aspect of the present invention, the sulfa drug is chemically bonded with a dye having a pK value of 4.0 to 9.0.

DETAILED DESCRIPTION OF THE PREFERRED EMBODIMENTS

The present inventiors made extensive studies in order to resolve the problems of conventional body fluid purification apparatuses and to develop a body fluid purification medium capable of selectively adsorbing pathogenic substances in blood. Based on these studies, the present inventors found out that this object can be achieved by fixing a sulfa drug on a surface of an insoluble support.

The sulfa drug used in the present invention is a chemotherapeutic agent also called a sulfonamide and can be represented by a general formula:

(wherein $R^1$ is methylene, $R^2$ is hydrogen, methylcarbonyl, guanidine, pyridine, 1,3-diazine, merazine, methazine, isomidine, azole (e.g., thiazole or isoxazole), or a derivative thereof, and a is 0 or 1).

Examples of a sulfa drug may include sulfanilamide, acetosulfamine, sulfapyridine, sulfaguanidine, sulfadiazine, sulfamerazine, sulfamethazine, sulfisoxazole, homosulfamine, sulfisomidine, sulfathiazole, sulfamethizole, sulfisomezole, phtyalysulfathiazole, and sulfadimethoxine. Preferred examples of the sulfa drug may include $N^1$-heterocyclic sulfa drugs, in particular, those having azole as the heterocyclic ring, e.g.: sulfathiazole, sulfamethizole, or sulfisomezole.

A sulfa drug as used herein may be chemically bonded with a dye having a pK value of 4.0 to 9.0. Dyes having a pK value of 4.0 to 9.0 are those having pK values of 4.0 to 9.0 among various indicators and histochemical dyes described in H.J. Conn's Biological Stains, R. D. Lillie, The Williams & Wilkins Company, Baltimore, 1977. A selected dye preferably has a pK value substantially equal to the isoelectric point of a target pathogenic substance and this corresponds to the pK range described above.

Preferred examples of such a dye may include lacmoid (7-amino-3,6-bis(m-dihydroxyphenyl)-2-phenexazone), phenol red (3,3-bis(p-hydroxyphenyl)-3H-2,1-benzoxathiole 1,1-dioxide and brilliant yellow represented by a formula:

In order to chemically bond a sulfa drug and a dye, the following procedures can be taken. First, 5 m mole of a dye is dissolved in 50 ml of a 5N aqueous solution of sodium hydroxide, and 5 ml of epichlorohydrin and 5 ml of N,N-dimethyformamide are added. The mixture is reacted in a water bath at 50° C. for 2 to 3 hours. Further, the reaction mixture is stirred overnight using a blood mixer (Type BM-101 available from kayagaki Irika Kogyo, Japan). Then, pH of the reaction mixture is adjusted to 7 to 8, and 50 ml of chloroform is added. The mixture is vigorously shaken, and water-insoluble materials are removed by extraction. In this operation, the insoluble materials as the upper layer is dissolved by addition of a small amount of N,N-dimethylformamide.

The thus obtained solution of epoxydized dye is bonded with the insoluble support treated with a silane coupling agent, utilizing the epoxy groups on the dye. The remaining epoxy groups are reacted with the sulfa drug. In this reaction, the sulfa drug is dissolved at a concentration of 100 mM in a mixture of N,N-dimethyformamide and 0.2M carbonate buffer solution of pH 10 at a volume ratio of 2:3. The solution of the sulfa drug is subjected to the reaction with the expoxy groups on the dye in a water bath at 80° C. for 3 to 5 hours, and the reaction mixture is further stirred overnight using the blood mixer. Thus, the sulfa drug is chemically bonded with the dye and is fixed on the support.

When the sulfa drug is chemically or covalently bonded with the dye, the effect of a dye ligand chromatography can be obtained. The dye ligand changes in its steric structure or electrostatic property by pH, and is most strongly bonded with the molecules to be eliminated at a pH value close to its pK value. The dye ligand has a freeness in its electric charge, hydrophobic property and steric configuration layer than an ion-exchanging functional group, and has a three-dimensional bondability rather than unidimensional bondability of an ion exchanger.

The azole ring in a sulfa drug exhibits hydrophobic property, while the hetero atom in the ring has a lone pair of electrons and serves as a proton acceptor. The sulfonamide portion of the sulfa drug has hydrogen bondability. The hydrophobic property of a main portion of the sulfa drug, the electrostatic property of the hetero atom, and hydrogen bondability near the main portion interact with the amino acid residue which constitutes a portion to be adsorbed in a pathogenic substance, in particular, globulin. Further, since the steric structure of the sulfa drug suitably fits with the molecular pocket of the globulin, good adsorption performance of a pathogenic substance is postulated to be obtained.

The insoluble support for fixing an adsorbent containing a sulfa drug as described above can be a hydrophobic or hydrophilic support.

The insoluble support can be in the form of granules, fibers, hollow fibers, membranes or the like. However, in view of easy passage of blood or plasma and easy handling during preparation of an adsorbent, a granular support is particularly preferable.

The granular support preferably has an average particle size of 0.05 to 5 mm. The average particle size is rated by sieving through sieves of different meshes defined in accordance with JIS-Z-8801, calculating an intermediate value between the largest and smallest sizes in each different mesh as the size of each mesh, and calculating an average particle size as a weight average of the intermediate values of the respective meshes. Although the shape of particles is preferably spherical to avoid damaging cells and occurrence of chipping or the like, the shape is not particularly limited.

Examples of granular supports may include organic high-molecular weight substances such as agarose, dextran, cellulose, polyacrylamide, polyvinyl alcohol, polyvinyl pyrrolidone, polyacrylonitrile, a styrene-divinylbenzene copolymer, polyethylene, polyacrylic ester, polymethacrylic ester, polyethylene, polypropylene, polyethylene tetrafluoride, an ethylenevinyl acetate copolymer, polyamide, polycarbonate, polyvinylidene fluoride, polyvinylformal, polyacrylate, polyether sulfone and activated carbon; and inorganic materials such as glass, alumina, titanium, and ceramics. A particularly good effect is obtained with a porous polymer, porous glass or silica gel. Examples of such a polymer may include known polymers of a porous structure such as polyamide, polyester, polyurethane, and polymers of vinyl compounds. Known supports normally used in immobilized enzymes or affinity chromatography can be used without limitation.

Among these porous supports, spherical silica gel is preferable due to excellent mechanical strength and chemical inertness, a large surface area, and good workability.

Porous particles to be used herein must be able to fix a sulfa drug adsorbent and preferably have an average pore size of 100 to 5,000 Å more and preferably 200 to 3,000 Å.

The porous structure preferably has an average pore size of 100 to 5,000 Å as described above. If the average pore size is smaller than 100 Å, the amount of a pathogenic substance adsorbed is small. If the average pore size is larger than 5,000 Å, the strength of porous particles is impaired, and the surface area is reduced.

The average pore size is measured with a mercury pressure porosimeter. Utilizing the porosimeter, mercury is pressed into a porous body, the pore volume is calculated in accordance with the introduced mercury amount, and the pore diameter is calculated from the pressure required for the porous body to introduce mercury.

The method for fixing a sulfa drug adsorbent on the surface of an insoluble support may be one of known methods using covalent bonds, ion bonds, physical adsorption or embedding or precipitation/non-solubility treatment. In order to prevent elution of a fixed adsorbent, the adsorbent is preferably fixed and rendered insoluble by covalent bonds. For this purpose, a known method of activating an insoluble support or bonding a ligand used in immobilized enzyme or affinity chromatography can be used. If required, a molecule of a suitable length (spacer) can be inserted between an insoluble support and a ligand. These fixing methods are described in, e.g., C. Baum, Biotechnol. Bioeng., 17, 253 (1975); G. Manecke, H. G. Vogt, Biochimie, 62, 603 (1980); D. L. Lappi, F. E. Stolzenbach, et al., Biochem. Biophys. Res. Commun., 69, 878 (1976); T. Watanabe, M. Fujimura, et al., J. Appl. Biochem., 1, 28 (1979); T. M. S. Chang, "Biomedical Applications of Immobilized Enzymes and Proteins", Plenum Press, New York, 1977; P. Cuatrecasas, I. Parikh, Biochem., 11, 2291 (1972); I Matsumoto; Y. Mizuno, et al., J. Biochem., 85, 1091 (1979); and L. Sundberg and J. Porath, J. Chromatography, 90, 87 (1974).

In accordance with a particularly preferable method, a silane coupling agent having a sulfa drug bonding functional group (e.g., a glycidyl group) is used. Examples of such silane coupling groups may include $\gamma$-glycidoxypropyltrimethoxysilane and $\beta$-(3,4-epoxycyclohexyl)ethyltrimethoxysilane. In order to fix a sulfa drug adsorbent, a support, e.g., a silica gel support is treated with an aqueous solution of a silane coupling agent so as to introduce epoxy groups in the surface of the support. The support and the sulfa drug adsorbent are reacted in a suitable medium (e.g., N,N-dimethylformamide or 1,4-dioxane) using a suitable catalyst (e.g., tributylamine and pyridine) at 50 to 90° C. The reaction time is selected to be 3 to 7 hours. After the reaction, non-reacted epoxy groups are blocked with ethanolamine or the like. In this manner, the sulfa drug adsorbent is firmly fixed in the surface of a carrier and will not elute into a body fluid upon contact therewith.

A body fluid purification medium according to the present invention can be used to adsorb and remove an unnecessary substance by the batch method by bringing the medium into contact with a body fluid. However, the body fluid purification medium is preferably used in a body fluid purification apparatus as described above.

In a body fluid purification apparatus of the present invention, a pathogenic substance purification medium is held and filled in a container having body fluid inlet and outlet ports.

The material of the container can be glass, stainless steel, polyethylene, polypropylene, polycarbonate, polystyrene, polymethylmethacrylate or the like. However, polypropylene or polycarbonate is particularly preferable since it can be sterilized by autoclave sterilization and is easy to handle. The container also preferably has a filter between a purification medium layer and inlet/output ports, the filter being capable of passing a body fluid therethrough but not the purification medium. The material of the filter is not particularly limited provided it is physiologically inactive and has a high mechanical strength. However, polyester or polyamide is preferably used.

The apparatus of the present invention will be described in more detail with reference to the accompanying drawings.

Figure 1:
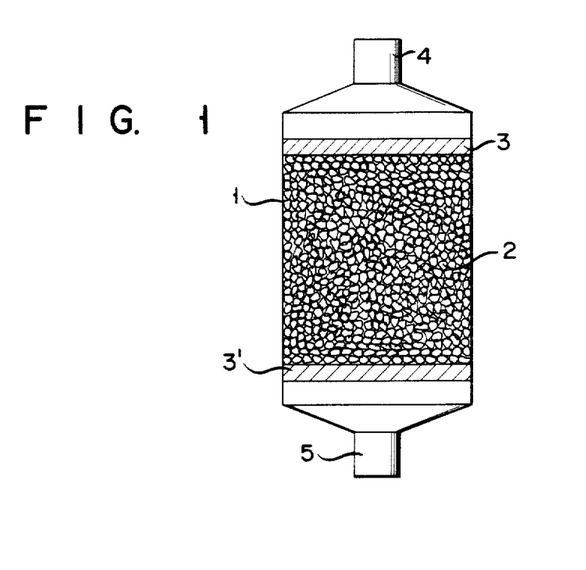
FIG. 1 is a schematic sectional view showing a body fluid purification apparatus according to the present invention.

FIG. 1 is a sectional view showing an embodiment of a body fluid purification apparatus of the present invention. A body fluid is introduced through a body fluid inlet port 4, treated with a body fluid purification medium 2 housed in a container or column 1, and flows out from a body fluid outlet port 5. The purification medium is held in the column by filters 3 and 3'.

Figure 2:
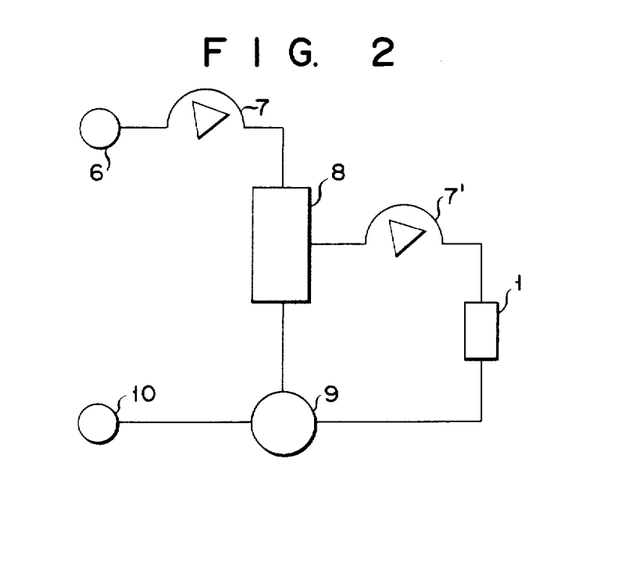
FIG. 2 is a diagram for explaining the purification process of a body fluid using the body fluid purification apparatus according to the present invention.

FIG. 2 is a schematic diagram illustrating an example of body fluid purification therapy using the body fluid purification apparatus of the present invention. Blood is introduced from a blood inlet port 6, supplied to a plasma separation unit 8 through a pump 7, and separated into blood cells and plasma. The separated plasma is supplied to a purification medium holding column (body fluid purification apparatus) 1 through a pump 7' to be subjected to adsorption treatment thereby, and is thereafter mixed with the blood cells by a plasma/blood cell mixing unit 9. The blood then flows out from a blood outlet port 10. When the apparatus of the present invention is used extracorporeally, the following two methods can be used. According to the first method, blood sampled from a patient's body is separated into plasma and blood cell components by a centrifugal, membrane or hollow fiber plasma separator. The plasma component is passed through the apparatus of the present invention to be purified, and mixed with the blood cell component. The mixture is then returned to the patient's body. According to the second method, blood sampled from the patient's body is passed directly through the apparatus of the present invention and is purified.

As for the method of passing a body fluid, it can be continuously or discontinuously passed in accordance with clinical conditions or other equipment conditions.

Before the body fluid purification apparatus of the present invention is used, it is charged with a physiological saline solution and is sterilized by autoclave sterilization.

The body fluid purification medium and the body fluid purification apparatus of the present invention can remove, from body fluids, pathogenic substances such as normal immunoglobulins (A, D, E, G and M); rheumatoid factors; antinuclear antibody; anti-DNA antibody; antilymphocyte antibody; antierythrocyte antibody; antiplatelet antibody; antiacetylcholine-receptor antibody; anti-large intestine autoantibody; anti glomerulus lung basement membrane antibody; anti desmosome for spinosum epidermic cells antibody; anti insulin receptor antibody; anti myelin antibody; anti factor VIII for hemophilia antibody; immunoglobulin derivatives such as reduced products or chemically modified products of immunoglobulins; a complex substance of immunoglobulins or of an immunoglobulin and another substance, in particular of an antigen and an antigen-like substance; complement; fibrinogen and the like.

The present invention will be described by way of its Examples below.

EXAMPLES 1–9 AND COMPARATIVE EXAMPLES 1–3

4 g of silica gel spheres (particle size distribution of 74 to 149 $\mu$m and a surface area of 87 $m^2$/g and available from Fuji Davison Chemical K.K.) having an average pore size of 460 Å were added to 40 ml of an aqueous solution of 5 w/v% $\gamma$-glycidoxypropyltrimethoxysilane (silane coupling agent) adjusted to a pH of 9 by pottasium hydroxide. The mixture was stirred with Blood Mixer at room temperature for 20 minutes and was dried in an oven at 150° C. for 45 minutes. The dried silica gel spheres were washed with distilled water and again dried at 120° C. under a reduced pressure for 3 hours. The epoxy groups on the silica gel spheres were reacted with sulfa drugs shown in Table 1 using tri-n-butylamine and pyridine as catalysts. Specifically, the silica gel spheres thus treated were added to 40 ml of a 100 mM solution of the sulfa drug in a mixed solvent of N,N-dimethylformamide and a 0.2M carbonate buffer solution of pH 10 in a volume ratio of 2:3. Tri-n-butylamine and pyridine were added to the mixture in an amount of each of 1 v/v%. The resultant mixture was reacted in a water bath at 80° C. for 3 hours. The reaction product (silica gel spheres) was washed with distilled water and the non-reacted epoxy groups were blocked using 1M ethanolamine. The resultant purification medium was repeatedly cleaned using a 0.02M acetate buffered saline of pH 4 and a 0.2M carbonate buffer of pH 10, cleaned with distilled water, dried at a reduced pressure at 120° to 150° C. for 3 hours or more, and tested for adsorption performance. Media of Comparative Examples were similarly tested using spherical silica gel in which phenylalanine as hydrophobic amino acid was similarly fixed, spherical silica gel in which 2-aminothiazole was similarly fixed, and spherical silica gel which was not subjected to a surface treatment.

The adsorption test was performed in the following manner. A glass test tube ("Larbo" of 15.5 mm diameter × 100 mm length; available from Terumo Corporation) was charged with a mixture of 0.5 g of each purification medium and 2 ml of a 0.1M phosphate buffered saline of pH 7.4. After the mixture was deaerated with an aspirator ("A-2S" from Tokyo Rikakikai K.K.), 3 ml of cow plasma containing 5 units/ml of heparin as an anticoagulant were added. Incubation was performed in a hot air circulating type thermostat ("P(S)-212" available from Tabai K.K.) at 37° C. for 90 minutes while stirring the mixture with a blood mixer ("BM-101" available from Kayagaki Irika Kogyo K.K.). The distal end of a main body of a disposable syringe (available from Terumo Corporation) having a volume of 5 ml was cut, and a 250-mesh nylon filter was mounted on the cut end. A silicone rubber stop having a stainless steel pipe extending therethrough was pressed into the end to provide a column. After the column was charged with the test tube contents, the contents were cleaned with 6 ml of a 0.1M phosphate buffered saline of pH 7.4, and the liquid flowing out the column was recovered.

The amount of albumin and total amount of proteins in the flowing liquid were determined by the bromcresol green method and the biuret method so as to determine the globulin amount as the difference between the total protein and albumin amount. For easy calculation, the globulin amount was assumed to be the protein amount other than the albumin, and for plasma, fibrinogen was also included in the globulins. The measurement values were subtracted from the albumin and globulin amounts of the flowing liquid obtained by not using an adsorbing medium in a similar manner, and the adsorption amounts in the respective adsorption media were calculated by equation (1). The adsorption amounts thus calculated were divided by the albumin or globulin amount of the flowing liquid obtained by not using an adsorption medium so as to calculate the adsorption rate by equation (2).

Adsorption amount (mg/g) = {(component amount in flowing liquid obtained not using 0.5 g of adsorption medium) − (component amount in flowing liquid obtained using adsorption medium)} × 2   (1)

Adsorption rate (%) = {(adsorption amount of equation (1))/(component amount in flowing liquid obtained not using adsorption medium)} × 100   (2)

The amount of immunoglobulin G (IgG) in the flowing liquid was measured by the single radial immunodiffusion method (SRID) so as to determine the IgG adsorption amount in a similar manner.

The obtained results are shown in Table 1. It is seen from Table 1 that purification media wherein sulfa drugs especially sulfamine, sulfapyridine, sulfathiazole, sulfamethizole, and sulfisomezole are bonded can selectively and effectively adsorb globulins and IgG.

TABLE 1

|  |  | Adsorption Capacity (3 ml of plasma per g of adsorbent) | | | | | | Adsorption Selectivity |
|---|---|---|---|---|---|---|---|---|
|  |  | Adsorption Amount (mg/g) | | | Adsorption Rate (%) | | | Adsorption Amount Ratio |
|  |  | Alubumin | Globulin | IgG | Alubumin | Globulin | IgG | (Globulin/Albumin) |
| Example |  |  |  |  |  |  |  |  |
| 1 | Sulfamine (Sulfa drug) | 1 | 17 | 14 | 1 | 12 | 19 | 17.0 |
| 2 | Sulfapyridine (Sulfa drug) | 8 | 42 | 11 | 9 | 30 | 15 | 5.3 |
| 3 | Sulfathiazole (Sulfa drug) | 19 | 109 | 55 | 21 | 77 | 73 | 5.7 |
| 4 | Sulfadiazine (Sulfa drug) | 13 | 40 | 14 | 14 | 28 | 19 | 3.1 |
| 5 | Sulfisomidine (Sulfa drug) | 19 | 64 | 25 | 21 | 45 | 33 | 3.4 |
| 6 | Sulfamethizole (Sulfa drug) | 18 | 96 | 41 | 20 | 68 | 54 | 5.3 |
| 7 | Phthalylsulfathiazole (Sulfa drug) | 12 | 40 | 22 | 13 | 28 | 29 | 3.3 |
| 8 | Sulfadimethoxine (Sulfa drug) | 11 | 57 | 18 | 12 | 41 | 24 | 5.2 |
| 9 | Sulfisomezole (Sulfa drug) | 13 | 89 | 36 | 14 | 63 | 48 | 6.8 |
| Comparative Example |  |  |  |  |  |  |  |  |
| 1 | Phenylalanine (Amino acid) | 24 | 52 | 29 | 27 | 37 | 38 | 2.2 |
| 2 | 2-Aminothiazole | 27 | 54 | 25 |  |  |  | 2.0 |
| 3 | Silica gel | 45 | 99 | 41 | 50 | 70 | 54 | 2.2 |

EXAMPLES 10–14 AND COMPARATIVE EXAMPLE 4

The adsorption test was performed following the same procedures as in Examples 1 to 9 except that human blood plasma was used in place of cow plasma.

The obtained results are shown in Table 2. It is seen from Table 2 that good adsorption performance and selectivity of globulins and IgG are obtained with purification media wherein sulfa drugs especially sulfathiazole, sulfamethizole and sulfisomezole are bonded.

TABLE 2

|  |  | Adsorption Capacity (3 ml of plasma per g of adsorbent) | | | | | | Adsorption Selectivity |
|---|---|---|---|---|---|---|---|---|
|  |  | Adsorption Amount (mg/g) | | | Adsorption Rate (%) | | | Adsorption Amount Ratio |
|  | Sulfa Drug | Alubumin | Globulin | IgG | Alubumin | Globulin | IgG | (Globulin/Alubumin) |
| Example |  |  |  |  |  |  |  |  |
| 10 | Sulfapyridine | 1 | 18 | — | 1 | 21 | — | 18.0 |
| 11 | Sulfathiazole | 16 | 65 | 33 | 18 | 75 | 100 | 4.1 |
| 12 | Phthalylsulfathiazole | 14 | 49 | 12 | 16 | 56 | 36 | 3.5 |
| 13 | Sulfamethizole | 13 | 58 | 22 | 15 | 67 | 67 | 4.5 |
| 14 | Sulfisomezole | 12 | 52 | 17 | 14 | 60 | 52 | 4.3 |
| Com- | Silica Gel Alone | 46 | 53 | 19 | 52 | 61 | 58 | 1.2 |

EXAMPLE 15 AND COMPARATIVE EXAMPLE 5

Porous glass particles, "CPG-10-500", (average pore size: 515 Å; particle size distribution: 75 to 125 μm; surface area: 44.3 m²/g; available from Electronucleonics Co., Ltd.) were treated with the silane coupling agent of Examples 1-5 as in Examples 1-5.

5 m mole (1.77 g) of phenol red were dissolved in 50 ml of a 5N aqueous solution of sodium hydroxide, and 5 ml of epichlorohydrin and 5 ml of N,N-dimethylformamide were added thereto. The mixture was reacted in a water bath at 50° C. for 2.5 hours, and was then stirred overnight using the blood mixer of Examples 1-5. The mixture was adjusted to pH of 8 using hydrochloric acid and added with 50 ml of chloroform. The resultant mixture was vigorously stirred and the water insoluble materials were removed by extraction. The remaining insoluble materials were dissolved by addition of a small amount of N,N-dimethylformamide. Thus, the desired solution of epoxidized dye was prepared.

20 ml of the dye solution prepared above was added to 2 g of the glass particles treated above. The mixture was reacted in a water bath at 80° C. for 3 hours. The obtained glass particles were washed with water and N,N-dimethylformamide. To the washed particles 20 ml of 100 mM sulfathiazole solution in a mixed solvent of N,N-dimethylformamide and a 0.2M carbonate buffer solution of pH 10 in a volume ratio of 2:3, followed by 1 v/v% of tri-n-butylamine and 1 v/v% of pyridine. Thereafter, the same procedures were taken as in Examples 1-5, thus obtaining a desired purification medium.

The adsorption test was performed following the same procedures as in Examples 1-5. The obtained results are shown in Table 3. An adsorption medium in which a compound of sulfathiazole as a sulfa drug and phenol red as a dye was bonded exhibited excellent selective adsorption performance.

The body fluid purification medium and body fluid purification apparatus of the present invention can selectively and effectively adsorb and remove plasma proteins such as immune complexes and immunoglobulins as pathogenic substances in blood. The medium and apparatus also allow easy sterilization. Since the body fluid purification medium of the present invention has a sulfa drug as a chemo therapeutic drug used for various therapies bonded thereto, it has a high standard of safety.

The present invention can be applied to normal therapies for purifying and regenerating blood and is particularly effective in safe and reliable therapies associated with bioimmune functions, especially, for therapies of hepatic insufficiency, autoimmune disease, renal disease, myoneural disease, blood dyscrasia, endocrinopathy, cacochymia, allergies, rejections upon transplantation of organs, or cancers.

The application of a body fluid purification medium of the present invention is not limited to a therapeutic device filled in an apparatus but can be extended to a separation/purification adsorbent for immunoglobulins and immune complexes.

What is claimed is:

1. A body fluid purification medium comprising:
   an insoluble support; and
   an adsorbent including at least one sulfa drug and fixed on a surface of said insoluble support for adsorbing and removing a pathogenic substance in a body fluid, wherein said support comprises particles.

2. A medium according to claim 1 wherein the particles have an average particle size of 0.05 to 5 mm.

3. A medium according to claim 1, wherein said support is porous.

4. A medium according to claim 3, wherein said support has pores having a size of 10 to 500 nm.

5. A medium according to claim 3, wherein said support comprises a material selected from the group consisting of a polymer, glass, silica gel and alumina.

6. A body fluid purification medium according to claim 1, wherein the sulfa drug is one member selected from the group consisting of sulfathiazole, sulfamethizole, and sulfisomezole.

7. A body fluid purification medium according to claim 1, wherein said sulfa drug is represented by the formula:

TABLE 3

| | | Adsorption Capacity (3 ml of plasma per g of adsorbent) | | | | | | Adsorption Selectivity |
|---|---|---|---|---|---|---|---|---|
| | | Adsorption Amount (mg/g) | | | Adsorption Rate (%) | | | Adsorption Amount Ratio |
| | Adsorbent | Alubumin | Globulin | IgG | Alubumin | Globulin | IgG | (Globulin/Alubumin) |
| Example 15 | Compound of Sulfathiazole and Phehol Red | 11 | 40 | 23 | 20 | 36 | 30 | 3.6 |
| Comparative Example 5 | CPG-10-500 Alone | 17 | 35 | 14 | 20 | 32 | 19 | 2.1 | where R¹ is methylene, R² is hydrogen, methylcarbonyl, guanidine, pyridine, 1,3-diazine, merazine, methazine, isomidine, azole, or a derivative thereof, and a is 0 or 1.

8. A body fluid purification medium comprising:
an insoluble support; and
an adsorbent including at least one sulfa drug and fixed on a surface of said insoluble support for adsorbing and removing a pathogenic substance in a body fluid, wherein said sulfa drug is chemically bonded to a dye having a pK value of 4.0 to 9.0.

9. A medium according to claim 8, wherein the sulfa drug is one member selected from the group consisting of sulfathiazole, sulfamethizole, and sulfisomezole.

10. A medium according to claim 8, wherein the dye is one member selected from the group consisting of lacmoid, brilliant yellow and phenol red.

11. A medium according to claim 8, wherein said sulfa drug is represented by the formula:

where R¹ is methylene, R² is hydrogen, methylcarbonyl, guanidine, pyridine, 1,3-diazine, merazine, methazine, isomidine, azole, or a derivative thereof, and a is 0 or 1.

12. A medium according to claim 11, wherein said sulfa drug is sulfanilamide, acetosulfamine, sulfapyridine, sulfaguanidine, sulfadiazine, sulfamerazine, sulfamethazine, sulfisoxazole, sulfamethizole, sulfisomezole, phthalylsulfathiazole, sulfadimethoxine, sulfamine, sulfathiazole, or sulfisomidine.

13. A body fluid purification medium comprising:
an insoluble support; and
an adsorbent including at least one sulfa drug and fixed on a surface of said insoluble support for adsorbing and removing a pathogenic substance in a body fluid, wherein said adsorbent is fixed on the surface of said support by a silane coupling agent.

14. A body fluid purification medium according to claim 13, wherein the sulfa drug is a member selected from the group consisting of sulfathiazole, sulfamethizole, and sulfisomezole.

15. A medium according to claim 13, wherein said sulfa drug is represented by the formula:

wherein R¹ is methylene, R² is hydrogen, methylcarbonyl, guaridine, pyridine, 1,3-diazine, merazine, methazine, isomidine, azole, or a derivative thereof, and a is 0 or 1.

16. A body fluid purification apparatus comprising:
a container having body fluid inlet and outlet ports and a body fluid flow path provided between said ports, and
a body fluid purification medium provided in said flow path of said container, said body fluid purification medium comprising a support and an adsorbent including at least one sulfa drug and fixed on a surface of said support for adsorbing and removing a pathogenic substance in a body fluid, wherein said sulfa drug is chemically bonded to a dye having a pK value of 4.0 to 9.0.

17. An apparatus according to claim 16, wherein the sulfa drug is selected from the group consisting of sulfathiazole, sulfamethizole, and sulfisomezole.

18. An apparatus according to claim 16, wherein the dye is one member selected from the group consisting of lacmoid, brilliant yellow and phenol red.

19. An apparatus according to claim 16, wherein said body fluid purification medium is housed between a pair of filters arranged in said container.

20. An apparatus according to claim 16, wherein said sulfa drug is represented by the formula:

where R¹ is methylene, R² is hydrogen, methylcarbonyl, guanidine, pyridin 1,3-diazine, merazine, methazine, isomidine, azole, or a derivative thereof, and a is 0 or 1.

21. An apparatus according to claim 20, wherein said sulfa drug is sulfanilamide, acetosulfamine, sulfapyridine, sulfaguanidine, sulfadiazine, sulfamerazine, sulfamethazine, sulfisoxazole, sulfamethizole, sulfisomezole, phthalylsulfathiazole, sulfadimethoxine, sulfamine, sulfathiazole, or sulfisomidine.

22. A body fluid purification apparatus comprising:
a container having body fluid inlet and outlet ports and a body fluid flow path provided between said ports; and
a body fluid purification medium provided in said flow path of said container, said body fluid purification medium comprising a support and an adsorbent including at least one sulfa drug and fixed on a surface of said support for adsorbing and removing a pathogenic substance in a body fluid, wherein said support comprises particles.

23. An apparatus according to claim 23, wherein said support has an average particle size of 0.05 to 5 mm.

24. An apparatus according to claim 22, wherein said support is porous.

25. An apparatus according to claim 24, wherein said support has a pore size of 10 to 500 nm.

26. An apparatus according to claim 24, wherein said support comprises a material selected from the group consisting of a polymer, glass, silica gel and alumina.

27. An apparatus according to claim 22 wherein the sulfa drug is selected from the group consisting of sulfathiazole, sulfamethizole, and sulfisomezole 28. An apparatus according to claim 22, wherein said body fluid purification medium is housed between a pair of filters arranged in said container.

29. An apparatus according to claim 22, wherein said sulfa drug is represented by the formula:

wherein $R^1$ is methylene, $R^2$ is hydrogen, methylcarbonyl, guanidine, pyridine, 1,3-diazine, merazine, methazine, isomidine, azole, or a derivative thereof, and a is 0 or 1.

30. A body fluid purification apparatus comprising:
  a container having body fluid inlet and outlet ports and a body fluid flow path provided between said ports; and
  a body fluid purification medium provided in said flow path of said container, said body fluid purification medium comprising a support and an adsorbent including at least one sulfa drug and fixed on a surface of said support for adsorbing and removing a pathogenic substance in a body fluid, wherein said adsorbent is fixed to the surface of said support by a silane coupling agent.

31. An apparatus according to claim 30, wherein the sulfa drug is selected from the group consisting of sulfathiazole, sulfamethizole, and sulfisomezole.

32. An apparatus according to claim 30, wherein said body fluid purification medium is housed between a pair of filters arranged in said container.

33. An apparatus according to claim 30, wherein said sulfa drug is represented by the formula:

where $R^1$ is methylene, $R^2$ is hydrogen, methylcarbonyl, guanidine, pyridine, 1,3-diazine, merazine, methazine, isomidine, azole, or a derivative thereof, and a is 0 or 1.

* * * * *

UNITED STATES PATENT AND TRADEMARK OFFICE
CERTIFICATE OF CORRECTION

PATENT NO. : 4,725,355

DATED : February 16, 1988

INVENTOR(S) : Yuichi YAMAMOTO and Tadashi SAMESHIMA

It is certified that error appears in the above-identified patent and that said Letters Patent is hereby corrected as shown below:

Column 1, line 22, delete "diseases" and insert --disease--.

Column 1, line 36, delete "cortex, myonosus,".

Column 1, line 37, delete "diabetes, or psychoneurosis is".

Column 1, line 37, delete "Thereafter," and kindly insert --Therefore,--.

Column 3, line 7, delete "preferably" and kindly insert --preferable--.

Column 3, line 10, delete "SUMMRY" and kindly insert --SUMMARY--.

Column 3, line 31, after "body", kindly insert --fluid--.

Column 3, line 61, delete "inventiors" and kindly insert --inventors--.

Column 4, line 18, delete "phtyalysulfathiazole" and kindly insert --phthalylsulfathiazole--.

Column 5, line 55, delete "polyethylene" and kindly insert --polystyrene--.

IN THE CLAIMS:

Claim 20, line 31, delete "pyridin" and kindly insert --pyridine,--.

UNITED STATES PATENT AND TRADEMARK OFFICE
CERTIFICATE OF CORRECTION

PATENT NO. : 4,725,355

DATED : February 16, 1988

INVENTOR(S) : Yuichi Yamamoto and Tadashi SAMESHIMA

It is certified that error appears in the above-identified patent and that said Letters Patent is hereby corrected as shown below:

Claim 23, line 52, delete "23" and kindly insert -- 22 --.

Signed and Sealed this

Fifth Day of July, 1988

Attest:

DONALD J. QUIGG

Attesting Officer

Commissioner of Patents and Trademarks